United States Patent
Makohliso et al.

(10) Patent No.: US 10,018,639 B2
(45) Date of Patent: Jul. 10, 2018

(54) KITS FOR DETECTING BREAST OR OVARIAN CANCER IN A BODY FLUID SAMPLE AND USE THEREOF

(75) Inventors: Solomzi Makohliso, Pully (CH); Irmgard Irminger-Finger, Geneva (CH); Fernando Herrera, Peseux (CH)

(73) Assignee: BARD1 LIFE SCIENCES LIMITED, Perth (AU)

( * ) Notice: Subject to any disclaimer, the term of this patent is extended or adjusted under 35 U.S.C. 154(b) by 310 days.

(21) Appl. No.: 13/825,715

(22) PCT Filed: Sep. 23, 2011

(86) PCT No.: PCT/IB2011/054194
§ 371 (c)(1),
(2), (4) Date: Mar. 22, 2013

(87) PCT Pub. No.: WO2012/038932
PCT Pub. Date: Mar. 29, 2012

(65) Prior Publication Data
US 2013/0217047 A1  Aug. 22, 2013

(30) Foreign Application Priority Data
Sep. 24, 2010 (CH) .................. 1553/10

(51) Int. Cl.
| | |
|---|---|
| *G01N 33/68* | (2006.01) |
| *C07K 7/06* | (2006.01) |
| *C07K 7/08* | (2006.01) |
| *C07K 14/47* | (2006.01) |
| *G01N 33/574* | (2006.01) |

(52) U.S. Cl.
CPC ........... *G01N 33/6893* (2013.01); *C07K 7/06* (2013.01); *C07K 7/08* (2013.01); *C07K 14/4748* (2013.01); *G01N 33/57415* (2013.01); *G01N 33/57449* (2013.01)

(58) Field of Classification Search
CPC ... C07K 1/00; C07K 7/00; C07K 7/04; C07K 7/06; C07K 7/08; C07K 9/00; C07K 11/00; C07K 14/00; C07K 14/46; C07K 14/47; C07K 14/4778; G01N 1/00; G01N 33/00; G01N 33/48; G01N 33/50; G01N 33/53; G01N 33/574; G01N 2033/57403; G01N 33/57407; G01N 33/57415; G01N 33/57449
See application file for complete search history.

(56) References Cited

U.S. PATENT DOCUMENTS

2007/0083334 A1 * 4/2007 Mintz et al. .................. 702/19

FOREIGN PATENT DOCUMENTS

| WO | WO 2004/113566 | 12/2004 |
| WO | WO 2008/119802 | 10/2008 |

OTHER PUBLICATIONS

Nowak et al. (Przeglad Menopauzalny=Menopause Review 14(4): 254-259, published online Nov. 27, 2015).*
Cole et al. (Proteomics Clin. Appl. 7: 17-29, 2013).*
Brzovic, P. S. et al. "Structure of a BRCA1-BARD1 heterodimeric RING-RING complex" *Nature Structural Biology*, Oct. 2001, pp. 833-837, vol. 8, No. 10.
Hansen, M. H. et al. "Antigen-Specific IgG Antibodies in Stage IV Long-Time Survival Breast Cancer Patients," *Molecular Medicine*, Jan. 1, 2001, pp. 230-239, vol. 7, No. 4.
Li, L. et al. "Oncogenic BARD1 Isoforms Expressed in Gynecological Cancers," *Cancer Research*, Dec. 15, 2007, pp. 11876-11885, vol. 67, No. 24.
Luborsky, J. L. et al. "Anti-Tumor Antibodies in Ovarian Cancer," *American Journal of Reproductive Immunology*, Aug. 1, 2005, pp. 55-62, vol. 54, No. 12.
Tang, Y. et al. "Detection of Circulating Anti-Mucin 1 (MUC1) Antibodies in Breast Tumor Patients by Indirect Enzyme-Linked Immunosorbent Assay Using a Recombinant MUC1 Protein Containing Six Tandem Repeats and Expressed in *Escherichia coli*," *Clinical and Vaccine Immunology*, Dec. 2010, pp. 1903-1908, vol. 17, No. 12.
Written Opinion in International Application No. PCT/IB2011/054194, dated Jul. 11, 2012, pp. 1-10.
Easton, D.F. et al., "Genetic Linkage Analysis in Familial Breast and Ovarian Cancer: Results from 214 Families," *Am. J. Hum. Genet.*, 1993, pp. 678-701, vol. 52, No. 4.
Kulasingam, V. et al., "Integrating high-throughput technologies in the quest for effective biomarkers for ovarian cancer," *Nature Reviews, Cancer*, May 2010, pp. 371-378, vol. 10.
Menon, U. et al., Sensitivity and specificity of multimodal and ultrasound screening for ovarian cancer, and stage distribution of detected cancers: results of the prevalence screen of the UK Collaborative Trial of Ovarian Cancer Screening (UKCTOCS), *Lancet Oncology*, Apr. 2009, pp. 327-340, vol. 10.
Wooster, R. et al., "Localization of a Breast Cancer Susceptibility Gene, BRCA2, to Chromosome 13q12-13", *Science*, Sep. 30, 1994, pp. 2088-2090, vol. 265, No. 5181.

* cited by examiner

*Primary Examiner* — Alana Harris Dent
(74) *Attorney, Agent, or Firm* — Rothwell, Figg, Ernst & Manbeck, P.C.

(57) ABSTRACT

The present invention relates to a method for the accurate, rapid and sensitive detection of breast or ovarian cancers from body fluid samples of a mammalian subject and related assay, kits and peptides suitable for such a method.

8 Claims, 5 Drawing Sheets

SEQUENCE LISTING

```
<160> NUMBER OF SEQ ID NOS: 12

<210> SEQ ID NO 1
<211> LENGTH: 15
<212> TYPE: PRT
<213> ORGANISM: Artificial sequence
<220> FEATURE:
<223> OTHER INFORMATION: Peptide p2
<220> FEATURE:
<221> NAME/KEY: MISC_FEATURE
<222> LOCATION: (15)..(15)
<223> OTHER INFORMATION: Xaa is or may be a Cysteine or can be absent

<400> SEQUENCE: 1

Glu Gly Gly Thr Met Pro Asp Asn Arg Gln Pro Arg Asn Arg Xaa
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Peptide p8
<220> FEATURE:
<221> NAME/KEY: MISC_FEATURE
```

```
<222> LOCATION: (15)..(15)
<223> OTHER INFORMATION: Xaa may be a Cysteine or be absent

<400> SEQUENCE: 2

Ile Leu Ser Arg Lys Pro Lys Pro Asp Ser Asp Val Thr Gln Xaa
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: Peptide p11
<220> FEATURE:
<221> NAME/KEY: MISC_FEATURE
<222> LOCATION: (1)..(1)
<223> OTHER INFORMATION: Xaa may be a Cysteine or be absent

<400> SEQUENCE: 3

Xaa Ser Val Met Asn Thr Gly Gln Arg Arg Asp Gly Pro Leu
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Peptide p13
<220> FEATURE:
<221> NAME/KEY: MISC_FEATURE
<222> LOCATION: (14)..(14)
<223> OTHER INFORMATION: Xaa may be a Cysteine or absent

<400> SEQUENCE: 4

Val Ala Tyr His Ala Arg Pro Asp Ser Asp Gln Arg Phe Xaa
1               5                   10

<210> SEQ ID NO 5
<211> LENGTH: 15
<212> TYPE: PRT
<213> ORGANISM: Artificial
<220> FEATURE:
<223> OTHER INFORMATION: Peptide p16
<220> FEATURE:
<221> NAME/KEY: MISC_FEATURE
<222> LOCATION: (15)..(15)
<223> OTHER INFORMATION: Xaa is or may be a Cysteine or absent

<400> SEQUENCE: 5

Asp Asn Glu Leu Ser Asp Leu Lys Glu Asp Lys Pro Arg Lys Xaa
1               5                   10                  15

<210> SEQ ID NO 6
<211> LENGTH: 25
<212> TYPE: PRT
<213> ORGANISM: Artificial Sequence
<220> FEATURE:
<223> OTHER INFORMATION: Peptide p21
<220> FEATURE:
<221> NAME/KEY: MISC_FEATURE
<222> LOCATION: (25)..(25)
<223> OTHER INFORMATION: Xaa may be a Cysteine or may be absent

<400> SEQUENCE: 6

Pro Val Cys Tyr Thr Pro Ala Trp Ile Gln Asp Leu Lys Ile Asn Arg
1               5                   10                  15

Gln Leu Asp Ser Met Ile Gln Leu Xaa
            20                  25
```

<210> SEQ ID NO 7
<211> LENGTH: 10
<212> TYPE: PRT
<213> ORGANISM: Artificial Sequence
<220> FEATURE:
<223> OTHER INFORMATION: Peptide p24
<220> FEATURE:
<221> NAME/KEY: MISC_FEATURE
<222> LOCATION: (10)..(10)
<223> OTHER INFORMATION: Xaa may be a Cysteine or absent

<400> SEQUENCE: 7

Lys Ala Gly Arg Cys Arg Ile Ile Gly Xaa
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Peptide p25
<220> FEATURE:
<221> NAME/KEY: MISC_FEATURE
<222> LOCATION: (13)..(13)
<223> OTHER INFORMATION: Xaa may be a Cysteine or absent

<400> SEQUENCE: 8

Met Val Ala Val Pro Gly Pro Thr Val Ala Pro Arg Xaa
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Peptide p34
<220> FEATURE:
<221> NAME/KEY: MISC_FEATURE
<222> LOCATION: (11)..(11)
<223> OTHER INFORMATION: Xaa may be a Cysteine or absent

<400> SEQUENCE: 9

Leu Arg Cys Ser Arg Cys Asn Ile Phe Gly Xaa
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Peptide p35
<220> FEATURE:
<221> NAME/KEY: MISC_FEATURE
<222> LOCATION: (11)..(11)
<223> OTHER INFORMATION: Xaa may be a Cysteine or absent

<400> SEQUENCE: 10

Ala Ala Arg Val Gly Val Lys Ala Cys Leu Xaa
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Peptide p36
<220> FEATURE:
<221> NAME/KEY: MISC_FEATURE
<222> LOCATION: (10)..(10)
<223> OTHER INFORMATION: Xaa is or may be a Cysteine or is absent

```
<400> SEQUENCE: 11

Asp Asn Glu Leu Ser Gly Val Lys Ala Xaa
1               5                   10

<210> SEQ ID NO 12
<211> LENGTH: 11
<212> TYPE: PRT
<213> ORGANISM: Artificial
<220> FEATURE:
<223> OTHER INFORMATION: Peptide p37
<220> FEATURE:
<221> NAME/KEY: MISC_FEATURE
<222> LOCATION: (11)..(11)
<223> OTHER INFORMATION: Xaa may be a Cysteine or absent

<400> SEQUENCE: 12

His Ile Phe Cys Ser Asn Ile Phe Gly Leu Xaa
1               5                   10
```

KITS FOR DETECTING BREAST OR OVARIAN CANCER IN A BODY FLUID SAMPLE AND USE THEREOF

CROSS-REFERENCE TO RELATED APPLICATION

This application is the U.S. national stage application of International Patent Application No. PCT/IB2011/054194, filed Sep. 23, 2011.

SEQUENCE LISTING

The present application includes a Sequence Listing in electronic format. The Sequence Listing is entitled 4472103SequenceListingRev.txt, was created on 19 Mar. 2018 and is 5 kb in size. The information in the electronic format of the Sequence Listing is part of the present application and is incorporated herein by reference in its entirety.

FIELD OF THE INVENTION

The present invention relates to kits for detection of ovarian and breast cancers in a sample. In particular, the invention relates to kits and a method using those kits for the early diagnosis of breast and ovarian cancers in biological fluids such as human serum.

BACKGROUND OF THE INVENTION

Breast cancer is the most commonly diagnosed cancer in women after non-melanoma skin cancer, and is the second leading cause of cancer deaths after lung cancer. Clinical evaluations have established that mammography screening with or without clinical breast examination, may decrease breast cancer mortality. Therefore, mammography remains the gold reference standard today for breast cancer screening, however, it suffers from a variety of limitations such as radiation hazard, considerable patient discomfort, higher false readouts with denser breast tissue, sensitivity & specificity varies according to technician's skill (60-80%), and typically over-diagnoses. Currently used serum/blood biomarkers (e.g. CA27.29, CA15.3, CEA, HER-2) are mainly used in monitoring and surveillance due to poor sensitivity and specificity for other than those applications. Patient management following initial suspicion of breast cancer usually includes confirmation of the diagnosis, evaluation of stage of disease, surgical removal of the tumour tissue and selection of a therapy. The survival rate to breast cancer is over 90% when detected and treated early with existing therapies.

Ovarian cancer is the second most common gynaecological cancer and is the ninth most common cancer but is the fifth most deadly. In the USA, ovarian cancer occurs in 1 of 2'500 post-menopausal women and is the most lethal gynaecological malignancy, accounting for 5-6% of all cancer-related deaths (*Kulasingam et al., 2010, Nature Reviews, Cancer,* 10, 371-377). The main problem is that ovarian cancer does not usually lead to alarming symptoms. A large majority of patients have advanced cancer and widespread disease at presentation. This late detection of ovarian cancer explains why the overall survival rate for ovarian cancer is less than 40%, whereas that the survival rate is close to 90% when diagnosed at early stage. Furthermore, there is no effective screening test that can detect the disease in its early stages. For women at increased risk, prophylactic oophorectomy is usually considered after the age of 35 if childbearing is complete. Patients with clear cell histology appear to have a worse prognosis.

The most studied/used marker for ovarian cancer is CA125 which is a protein antigen found at abnormally high levels in the blood of many ovarian cancer patients, but was also found to be elevated in non-cancer cases (e.g. pregnant women). Furthermore, the CA125 biomarker was found to have a low sensitivity and specificity and is essentially used for monitoring response to treatment for ovarian cancer. Although CA125, has no prognostic significance when measured at the time of diagnosis, it seems to show a correlation with survival with the progression of the disease, especially when measured after the course of chemotherapy for patients with stage III or stage IV disease. Another method used for early detection of ovarian cancer is transvaginal ultrasound. However, this method is known to have a very low positive predictive value of about 3% according to a major recent study (*Menon et al.* 2009, *Lancet Oncol.,* 10, 327-40).

In most families affected with the breast and ovarian cancer syndrome or site-specific ovarian cancer, genetic linkage has been found to the BRCA1 locus on chromosome 17q21 (*Easton et al.,* 1993, *Am. J. Hum. Genet.,* 52 (4): 678-701). BRCA2, responsible for some forms of inherited ovarian and breast cancer, has been mapped by genetic linkage to chromosome 13q12 (*Wooster et al.,* 1994, *Science* 265 (5181): 2088-90, 1994). The majority of those women with those mutations presumably have family members with a history of ovarian and/or breast cancer; therefore, they may have be more vigilant and inclined to participate in cancer screening programs that may have led to earlier detection. However, for other women populations, early detection remains more uncertain.

Several tests using biomarkers in blood have attempted to make the diagnosis of ovarian (OC) and breast cancer (BC) less invasive, more accurate, less invasive or less risky than the use of known diagnostic tools, i.e. mammography for BC. However most of them have been discarded after a series of unfortunate misinterpretations or due to insufficient experimental evidence (*Kulasingam et al.,* 2010, above).

Therefore, there is an emerging need for developing new methods and tools for providing an easy, reliable (minimum sensitivity and specificity), non-invasive and early diagnosis of breast and/or ovarian cancers, before those cancer cause symptoms.

SUMMARY OF THE INVENTION

The present invention is directed towards to a method for detecting breast or ovarian cancers from a biological fluid sample of a mammalian subject and related assay, kits and peptides suitable for the detection of breast or ovarian cancers. In particular, the invention relates to the unexpected finding that peptides according to the invention used as antigens adsorbed on a solid surface allow the detection of endogenous antibodies in a blood sample from a subject, which are indicative of a breast or an ovarian cancer.

A first aspect of the invention provides a method for detecting a breast or an ovarian cancer from a biological fluid sample of a mammalian subject comprising the steps of:
  (a) providing a biological fluid sample from a mammalian subject;
  (b) bringing the said biological fluid sample into contact with a solid matrix where at least one peptide is bound to, wherein the contacting is under conditions sufficient for binding an antibody present in the said biological fluid sample to the said at least one peptide through antigen-antibody interactions and wherein the said at least one peptide has a sequence of amino acids of a peptide according to the invention or of any variant thereof;

(c) Removing the biological fluid sample for removing from the solid matrix any unbound antibody from the surface of the said solid matrix;

(d) Detecting the presence of an antigen-antibody complex bound to the said solid matrix, wherein the presence of the said complex is indicative that the biological fluid sample contains one or more breast or ovarian-cancer associated endogenous antibodies.

A second aspect of the invention provides a kit for detecting a biomarker for a breast or an ovarian cancer in a biological fluid sample, the kit comprising at least one peptide according to the invention or at least one variant thereof or a combination thereof.

A third aspect of the invention provides an isolated peptide according to the invention.

A fourth aspect of the invention provides an immunoassay preparation for the detection of a breast or ovarian cancer comprising at least one peptide according to the invention.

A fifth aspect of the invention provides a use of a peptide according to the invention in an assay for the detection of a breast or ovarian cancer.

A sixth aspect of the invention provides a use of a peptide according to the invention or of an immunoassay preparation according to the invention for the coating of a solid matrix for performing an immunoassay.

A seventh aspect of the invention resides in a use of a kit according to the invention for detecting a breast or an ovarian cancer from a biological fluid sample of a mammalian subject.

Other features and advantages of the invention will be apparent from the detailed description, figures and sequences.

DESCRIPTION OF THE FIGURES

In FIG. 1B, one sample (control 7) showed a significantly higher response than other control cases studies. It was unclear ultimately if this was due to an error or if indeed the corresponding control person had cancer. FIG. 1C shows results from four ovarian cancer cases (of which one was a remission case: sample 3) and four healthy controls that were carried out by an independent professional diagnostics laboratory. Overall the results were reproducible, with the remission case again clearly discernable.

In FIG. 2A, the LDA scores of the controls are grouped separately from those of breast cancer cases. In FIG. 2B, the scores of each sample group are shown separately, in order to allow to see how well the results/invention can separate malignant from benign tissue. FIG. 2C shows the Receiver Operating Curve (ROC) of results from the testing set. The ROC is obtained by plotting the sensitivity (or true positive rate) versus false positive rate (1-specificity) for a binary classification system (e.g. sick or healthy), as its discrimination threshold is varied. The area under the curve (AUC) of the ROC is a reflection of the performance of the binary classification system or test. A perfect test would result in an AUC=1. The ROC was plotted by varying the threshold (LDA score) as described in Example 3. By selecting a certain threshold LDA score, above which the result is considered positive (i.e., presence of cancer), the sensitivity was plotted (true positive rate) versus (1—specificity) leading to an AUC=0.92.

DETAILED DESCRIPTION OF THE INVENTION

Figure 1:
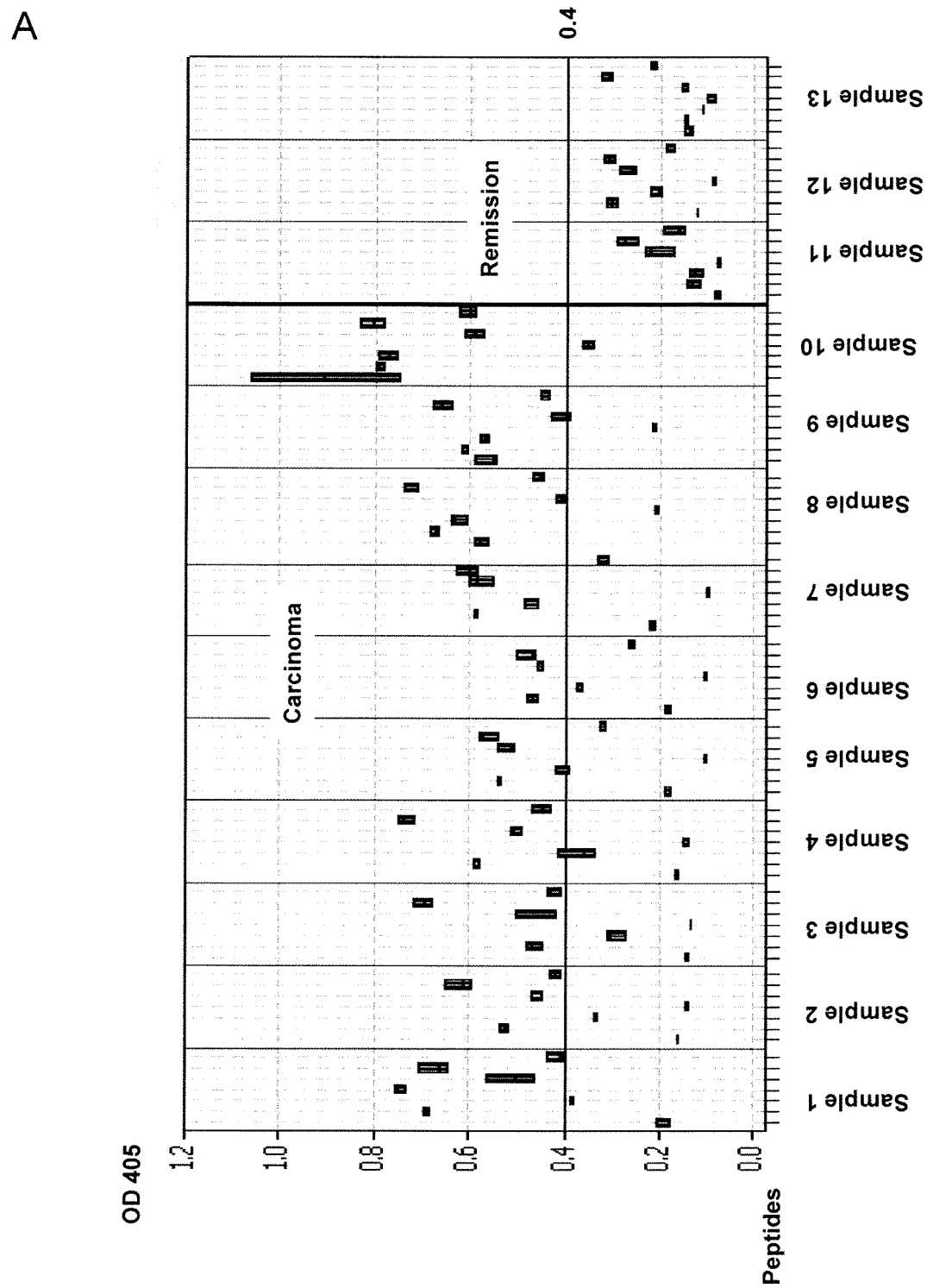
FIG. 1 shows the optical density (OD) measured at 405 nm from an inverse ELISA assay from one of the studies as described in Example 2 on thirteen blood samples of ovarian cancer (FIG. 1A) and seven controls, i.e. healthy samples (FIG. 1B) as described in Example 3. The x-axis represents the peptides used in the assay which are detailed in Table 2, as well as the notation identifying the samples. Boxes represent the variance of 3 measurements. The vertical lines divide the graph by sample and the horizontal line at $OD_{40.5\ nm}=0.4$ allows better visualization of the higher response from cancer samples versus controls. Note that in this study it was indeed possible to distinguish those patients in remission, as indicated in FIG. 1A (samples 11-13).
Figure 1:
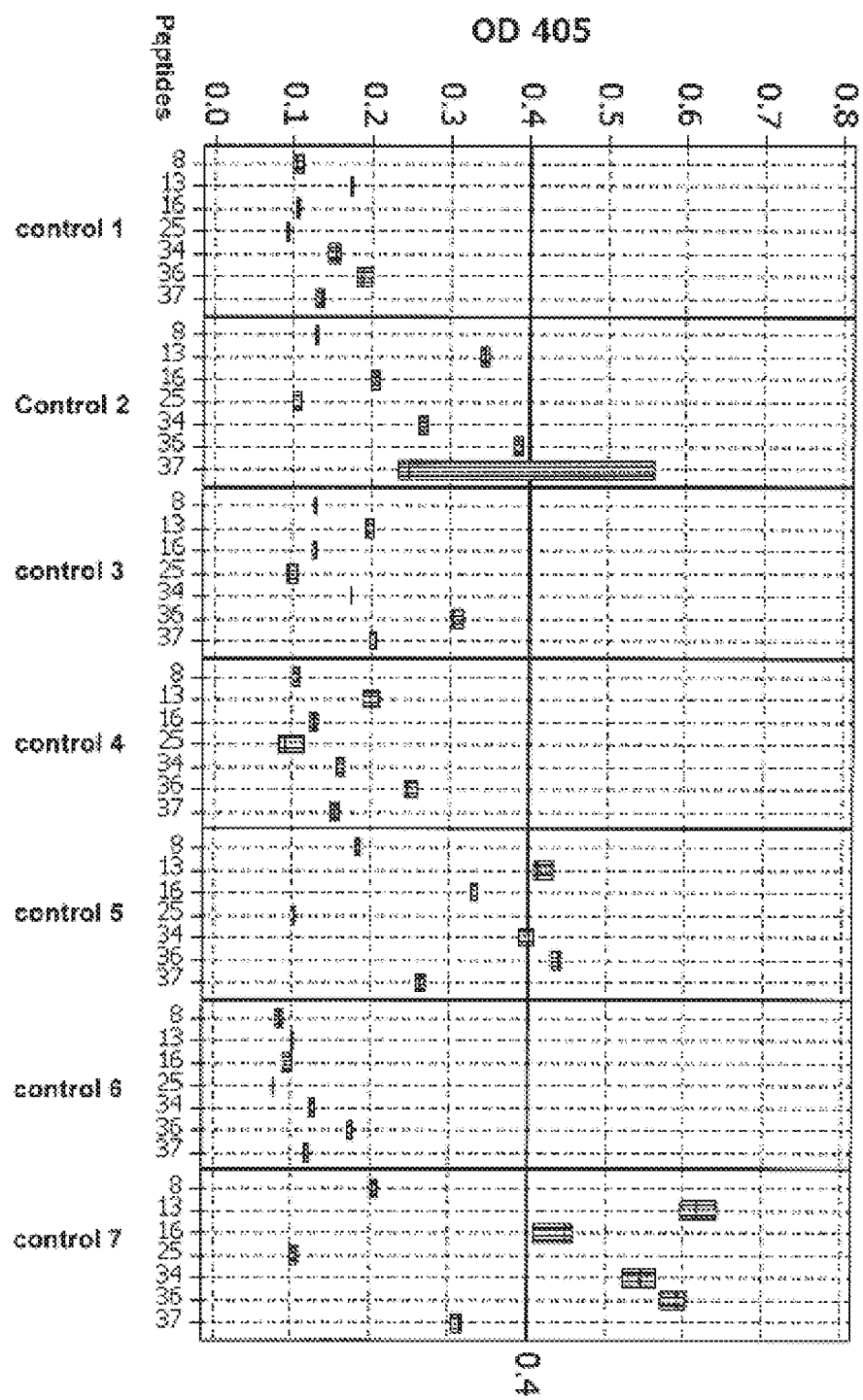
Figure 1:
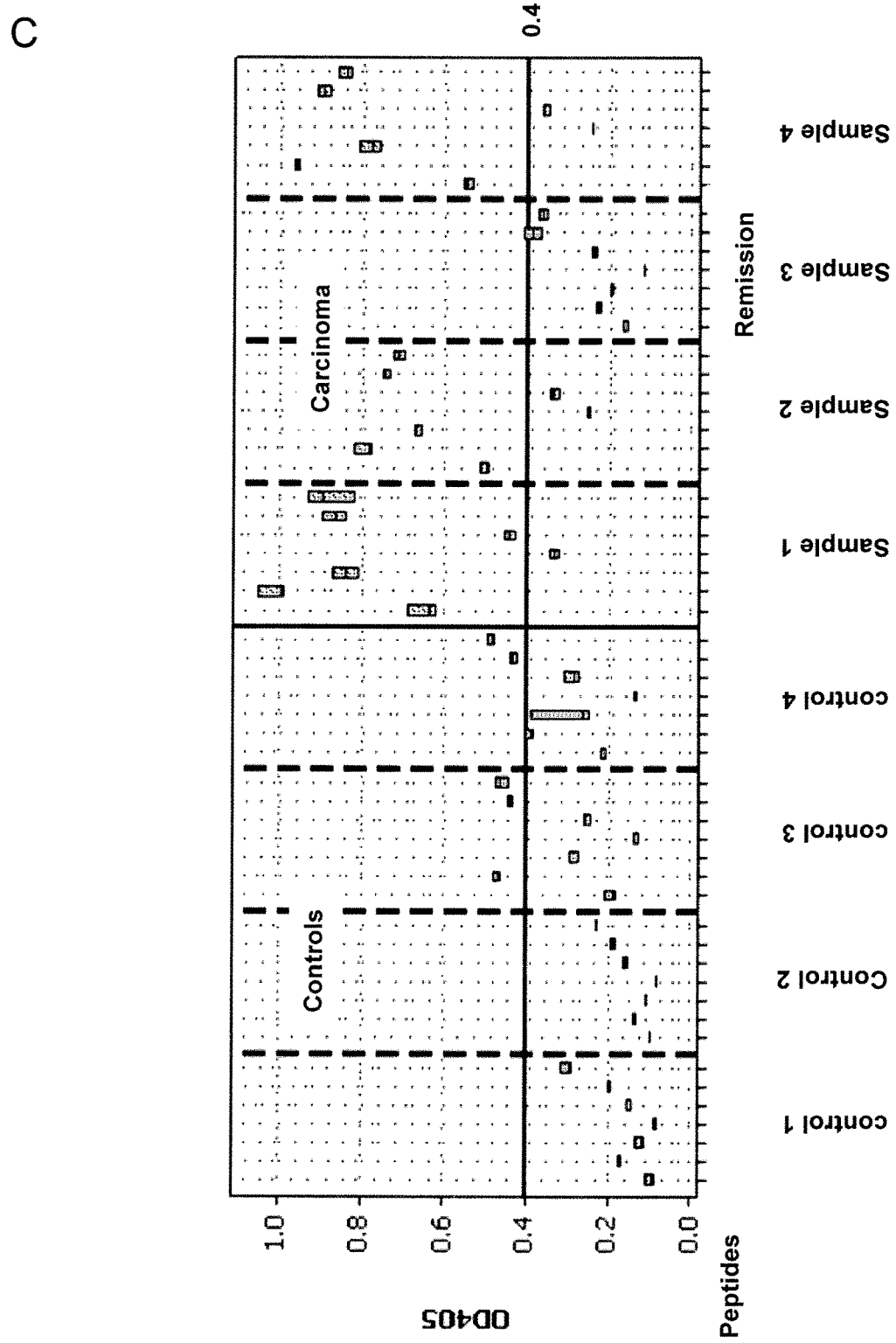

The term "subject" as used herein refers to mammals. For examples, mammals contemplated by the present invention include human, primates, domesticated animals such as cattle, sheep, pigs, horses and the like.

The term "isolated" is used to indicate that the molecule is free of association with other proteins or polypeptides, for example as a purification product.

The expression "breast cancer" includes malignant breast neoplasm, i.e. cancer originating from breast tissue, most commonly from the inner lining of milk ducts or the lobules that supply the ducts with milk.

The expression "ovarian cancer" includes any of various malignant neoplasms characterized by the proliferation of anaplastic cells that tend to invade surrounding tissue of ovaries and metastasize to new body sites. The pathological condition is characterized by such growths. For example, ovarian cancer includes ovarian clear cell carcinoma.

The expression "biological fluid sample" refers to a clinical fluid sample for testing which is taken from a body fluid from a mammal such as saliva, blood and urine. For example, a biological fluid sample is a serum sample from a human subject.

The expression "control sample" refers to a positive control or a negative control sample. A negative control sample includes a body fluid sample taken from a subject that is the same or homologous species as the subject to be assayed for autoantibodies and is known to have normal biological state, e.g. without detectable autoantibodies against at least one peptide according to the invention or a solution which does not contain antibodies that are immunoreactive with at least one peptide according to the invention. A negative control sample includes a sample taken from a control subject. A positive control sample includes a body fluid sample taken from a subject that is the same or homologous species as the subject to be assayed for autoantibodies and is known to have detectable autoantibodies against at least one peptide according to the invention or a solution which does contain antibodies that are immunoreactive with at least one peptide according to the invention.

The term "variant" as referred to herein, means a polypeptide substantially homologous to the original peptide sequence, but which has at least one an amino acid sequence different from that of the original sequence because of one or more deletions, insertions or substitutions. Substantially homologous means a variant amino acid sequence that is at least 80%, at least 85%, at least 90%, at least 95%, at least 96%, at least 97%, at least 98% or at least 99% identical to the original amino acid sequences, as disclosed above. The percent identity of two amino acid sequences can be determined by visual inspection and/or mathematical calculation, or more easily by comparing sequence information using known computer program used for sequence comparison such as Clustal package version 1.83. A variant may comprise a sequence having at least one conservatively substituted amino acid, meaning that a given amino acid residue is replaced by a residue having similar physiochemical characteristics. Generally, substitutions for one or more amino acids present in the original polypeptide should be made conservatively. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known (Kyte, et al, 1982, *J. Mol. Biol.*, 157: 105-131). For example, a "conservative amino acid substitution" may involve a substitution of a native amino acid residue with a non native residue such that there is little or no effect on the polarity or charge of the amino acid residue at that position. Desired amino acid substitutions (whether conservative or non-conservative) can be determined by those skilled in the art at the time such substitutions are desired. Exemplary amino acid substitutions are presented in Table 1 below:

TABLE 1

| Original residues | Examples of substitutions |
| --- | --- |
| Ala (A) | Val, Leu, Ile |
| Arg (R) | Lys, Gln, Asn |
| Asn (N) | Gln |
| Asp (D) | Glu |
| Cys (C) | Ser, Ala |
| Gln (Q) | Asn |
| Glu (E) | Asp |
| Gly (G) | Pro, Ala |
| His (H) | Asn, Gln, Lys, Arg |
| Ile (I) | Leu, Val, Met, Ala, Phe, Norleucine |
| Leu (L) | Ile, Val, Met, Ala, Phe, Norleucine |
| Lys (K) | Arg, Gln, Asn |
| Met (M) | Leu, Ile, Phe |
| Phe (F) | Leu, Val, Ile, Ala, Tyr |
| Pro (P) | Ala, Gly |
| Ser (S) | Thr, Ala, Cys |
| Thr (T) | Ser |
| Tyr (Y) | Trp, Phe, Thr, Ser |
| Val (V) | Ile Met, Leu, Phe, Ala, Norleucine |

The term "solid matrix" includes any solid phase support suitable for carrying out an immunoassay or a method according to the invention. It includes beads, microparticles, nanoparticles, tubes, fabrics or plates, films, slides, wells, formed from or coated with glass, polystyrene, polypropylene, nitrocellulose, quartz, ceramic, dextran or other materials. For example, the solid matrix is in a form of microtiter wells, such as a 96-well microtiter plate.

The expression "kit" comprises at least one polypeptide according to the invention or a variant thereof or a combination thereof as described herein to be coupled or already coupled to a solid matrix and optionally instructional material.

Peptides

According to one aspect of the invention, is provided an isolated peptide having at least 80% identity or homology with a sequence of amino acids selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 12.

In a further embodiment, is provided an isolated peptide having at least 90% identity or homology with a sequence of amino acids selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 12.

In another further embodiment, is provided an isolated peptide according to the invention having an amino acid sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 12.

Table 2 below presents the Sequence identity numbers and associated molecules:

TABLE 2

| SEQ ID NO. | Molecule |
| --- | --- |
| 1 (p2) | EGGTMPDNRQPRNR (C) |
| 2 (p8) | ILSRKPKPDSDVTQ (C) |
| 3 (p11) | (C) SVMNTGQRRDGPL |
| 4 (p13) | VAYHARPDSDQRF (C) |
| 5 (p16) | DNELSDLKEDKPRK (C) |
| 6 (p21) | PVCYTPAWIQDLKINRQLDSMIQL (C) |
| 7 (p24) | KAGRCRIIG (C) |
| 8 (p25) | MVAVPGPTVAPR (C) |
| 9 (p34) | LRCSRCNIFG (C) |
| 10 (p35) | AARVGVKACL (C) |
| 11 (p36) | DNELSGVKA (C) |
| 12 (p37) | HIFCSNIFGL (C) |

Synthetic chemistry methods, such as solid-phase peptide synthesis, can be used to synthesize the polypeptides according to the invention. Purification of those peptides may be carried out by means of any technique known in the art of protein/peptide purification. Exemplary techniques include ion-exchange chromatography, hydrophobic interaction chromatography, and immunoaffinity methods.

According to another embodiment, is provided an immunoassay preparation useful for the detection of a biomarker for a breast or an ovarian cancer in a biological fluid sample comprising at least one peptide according to the invention.

According to a further embodiment, is provided an immunoassay preparation useful for the detection of a biomarker for a breast cancer in a biological fluid sample comprising a combination of peptides according to the invention or of variants thereof. In particular, the combination comprises: a) at least one peptide selected from SEQ ID NO: 9 or SEQ ID NO: 12 or a variant thereof; and b) at least one peptide selected from SEQ ID NO: 5 or of SEQ ID NO: 10 or a variant thereof.

According to another further embodiment, is provided an immunoassay preparation useful for the detection of a biomarker for an ovarian cancer in a biological fluid sample a combination of peptides according to the invention or of variants thereof. In particular, the combination comprises: a) at least one peptide selected from SEQ ID NO: 9 or SEQ ID NO: 12 or a variant thereof; and b) at least one peptide selected from SEQ ID NO: 2 or of SEQ ID NO: 4 or a variant thereof.

According to another embodiment, is provided a use of an immunoassay preparation according to the invention for the coating of a solid matrix for performing an immunoassay.

Kit

According to another aspect of the invention, is provided a kit for detecting a biomarker for a breast or an ovarian cancer in a biological fluid sample, the kit comprising at least one peptide according to the invention or a variant thereof or a combination thereof.

According to a further aspect, the invention relates to a kit for carrying out a method according to the invention.

The kit according to the invention comprises at least one polypeptide according to the invention, a variant thereof or a combination thereof for coupling, or already coupled to a solid matrix as solid phase support as referred herein. Various solid matrices can be used, including but not limited to glass, polystyrene, polypropylene, nitrocellulose, quartz, ceramic, dextran or other materials. Suitable forms of the solid matrix include beads, microparticles, nanoparticles, tubes, fabrics or plates, films, slides, wells, formed from or coated with these materials. Typically, the solid matrix comprises microtiter wells, such as a 96-well microtiter plate.

The fixation of the peptides according to the invention to the solid matrix in a kit according to the invention may be carried out by adsorption or chemical coupling to a solid phase support. Any means known in the art for immobilizing a protein or peptide to a solid support can be used. The peptides according to the invention can be either covalently or non-covalently bound to the solid matrix by techniques such as covalent bonding via an amide or ester linkage or adsorption. Peptides can be bound using binding pairs such as biotin and avidin or antibody and antigen. After the peptides are affixed to the solid matrix, the solid matrix can be incubated with a blocking solution (containing a blocking protein such as bovine serum albumin) to reduce non-specific adsorption of antibodies in a test sample to the support surface. According to one aspect, the polypeptides according to the invention can be synthesized directly on the solid matrix of the kit of the invention.

According to one embodiment, when the kit comprises at least one polypeptide according to the invention, a variant thereof or a combination thereof for coupling to a solid matrix as solid phase support, the kit further optionally comprises coupling reagents and/or a solid matrix for performing an immunoassay.

According to another further embodiment, the kit according to the invention further comprises at least one rinsing reagent for washing unbound material before detection in order to avoid background noise detection. Typically rinsing reagents comprise standard buffers known in the art.

According to another further embodiment, the kit according to the invention further comprises at least one control sample optionally together with calibration information for quantification of detected autoantibodies.

Methods Using a Kit According to the Invention

According to another aspect, the invention provides a method for detecting a breast or an ovarian cancer from a biological fluid sample of a mammalian subject comprising the steps of:

(a) providing a biological fluid sample from a mammalian subject;
(b) bringing the said biological fluid sample into contact with a solid matrix where at least one peptide is bound to, wherein the contacting is under conditions sufficient for binding an antibody present in the said biological fluid sample to the said at least one peptide through antigen-antibody interactions and wherein the said at least one peptide has a sequence of amino acids of a peptide selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 12 and any variant thereof;
(c) Removing the biological fluid sample from the solid matrix for removing any unbound antibody from the surface of the said solid matrix;
(d) Detecting the presence of an antigen-antibody complex bound to the said solid matrix, wherein the presence of the said complex is indicative that the biological fluid sample contains one or more breast or ovarian-cancer associated autoantibodies.

According to a further embodiment, is provided a method according to the invention, wherein the said at least one peptide has a sequence of amino acids of a peptide selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10, SEQ ID NO: 11 and SEQ ID NO: 12.

According to another further embodiment, is provided a method according to the invention, wherein the said biological fluid sample is brought into contact with the said solid matrix under step b), where a combination of peptides or of variants thereof according to the invention is bound to said solid matrix.

According to another further embodiment, is provided a method for detecting a breast cancer from a biological fluid sample of a mammalian subject wherein the said biological fluid sample is brought into contact with the said solid matrix under step b), where a combination of peptides or of variants thereof is bound to the said solid matrix and where the combination comprises: a) at least one peptide selected from SEQ ID NO: 9 or SEQ ID NO: 12 or a variant thereof; and b) at least one peptide selected from SEQ ID NO: 5 or of SEQ ID NO: 10 or a variant thereof.

According to another further embodiment, is provided a method for detecting an ovarian cancer from a biological fluid sample of a mammalian subject wherein the said biological fluid sample is brought into contact with the said solid matrix under step b), where a combination of peptides or of variants thereof is bound to the said solid matrix and where the combination comprises: a) at least one peptide selected from SEQ ID NO: 9 or SEQ ID NO: 12 or a variant thereof; and b) at least one peptide selected from SEQ ID NO: 2 or of SEQ ID NO: 4 or a variant thereof.

According to another further embodiment, is provided a method according to the invention, wherein the method further comprises a step of comparing the signal obtained under the detection step d) with the same signal obtained for at least one control sample, wherein the signal obtained for the said at least one control sample is collected previously, simultaneously or posteriori to the detection step d) for the said biological fluid sample.

Detection of the captured/bound antibodies under step d) by any suitable method known in the art for detecting captured antibodies or proteins on surfaces such as optical detection (e.g. ELISA), mass variation detection (e.g. surface Plasmon resonance, mass spectrometry), electrical detection (e.g. impedance spectroscopy, electrochemical) techniques.

Results of the assay may be qualitative or quantitative. The amount of captured/bound antibodies associated with the solid matrix can be compared with positive and negative controls. The controls are typically run concomitantly with the sample to be tested. A positive control can be a serum or a solution containing antibodies that are immunoreactive with at least one peptide according to the invention. A negative control can be a serum or solution which does not contain antibodies that are immunoreactive with at least one peptide according to the invention. For quantization, a calibration curve using known quantities of antibody to at least one peptide according to the invention can be generated and/or used. Antibodies for use as positive controls may be produced using all, or fragments of, the amino acid sequence of a peptide according to the invention.

The comparison with normal healthy biological fluid samples may be achieved with different methods. According to one embodiment, it may be carried out by including a control reaction with a non-diseased blood sample. According to another embodiment, it may be carried out by employing a value for the concentration of the endogeneous antibody for a typical biological fluid sample from a healthy subject. Typically, the comparison of the level of endogeneous antibody present in a sample under investigation may be performed with respect to a value determined in each single testing procedure or to a predetermined value. The predetermined value may be determined for the testing procedure in general, or alternatively, the value may be valid only for a certain batch of testing reagents. For example, the reference value may be valid for a defined calibration period only and may be redefined upon calibration of the testing process.

The method, the kit and uses according to the invention may be suited for screening purposes as well as for diagnostic purposes and may be applied in primary diagnosis as well as in monitoring of disease course during or after treatment.

The invention having been described, the following examples are presented by way of illustration, and not limitation.

EXAMPLES

The following abbreviations refer respectively to the definitions below: kDa (Kilo Dalton), µg (microgram), µL (microliter), min (minute), M (molar), sec (second), BSA (bovine serum albumin), CCC (clear cell carcinoma), ELISA (Enzyme-linked immunosorbent assay), OD (optical density).

Example 1: Peptide Synthesis

Peptides were synthesized by standard peptide solid phase synthesis procedures known to those skilled in the art. Purity of the peptides was at least 80%. Peptides were dissolved in mother solution in 1 mg/mL in buffer and stored in aliquots of 200 mL at −20° C. Peptides were stored in buffer carbonate, pH 9.6.

Example 2: ELISA Immunoassay Using Peptides According to the Invention

The method according to the invention is exemplified in the form of an inverse ELISA assay as described in Example 2 where peptides according to the invention are adsorbed on the surface of a well plate and the presence of endogenous antibodies in the serum from patients is investigated as follows:

Plates

DINEX 3010 Immolux plates (Bioconcept, Switzerland) were used. Plates were coated with the peptides at a concentration of 10 µg/mL (100 µL/well) in carbonate buffer 0.05 M, pH 9.6, 2 wells per peptide and left incubated overnight at 4° C. 80 wells were coated with the peptides and 1 line was coated with a mixture of human IgG pooled from normal human sera (Southern Biotech) at 1:1000 in carbonate buffer for positive control tests and another line was left empty (no coating) to measure the non-specific binding (background) (negative control).

Procedure

The coated wells are then washed 3 times with 250 µL/well of PBST (0.05% Tween-20 in Phosphate buffer saline 0.15M, pH 7.4) to remove the coating solution. Wells are then incubated for 1 hour at 37° C. with BSA diluents/blocking solution (1% BSA in PBST, 0.1 g/L Methiolate) (300 µL/well). The blocking solution is then removed and the plate is washed 3 times with PBST. Human sera diluted at 1:70 in the BSA diluents/blocking solution is added (100 µL/well). The plate is then covered with an adhesive plastic and incubated for 2 h at 37° C. The solution is then removed and the plate is washed 3 times with PBST (250 µL/well). Horse radish-labeled antihuman antibody is added at a dilution of 1:1000 in the BSA diluents/blocking solution (100 µL/well) and incubated 1 h at 37° C. A substrate solution is then added to the well (100 µL/well) where coloration is obtained after about 2 min incubation and the well is further incubated for 5 min at room temperature (either 2-component ABTS substrate or TMB substrate). The reaction is stopped (quenching) by addition of $H_2SO_4$ at 2M (100 µL/well) and incubation during 2 min. The absorbance at 450 nm is red using a microtiter plate spectrophotometer. Signal cut off value was set at <0.1 OD.

Reagents

The protein detector HRP microwell kit, Anti-Human, 54-62-10, KPL, Inc. USA was used.

Peptides

Peptides used as antigens in the present reversed ELISA assay were those prepared according to Example 1.

Data Treatment

Data mining (detection of patterns within the data) was performed by software Matlab® from Mathworks Corp, Minitab® and SPSS® from IBM Corp.

Statistical Analysis

Statistical analysis was then performed by three different methods in parallel: Principal component analysis (PCA), Linear Discriminant Analysis (LDA), Hierarchical Cluster Analysis and Regression Model (*Pepe*, 2003, *"The Statistical Evaluation of Medical Tests for Classification and Prediction"*, Oxford University Press). For principal component analysis, data were grouped by class (patients, benign conditions and likely healthy people). A PCA was then carried out for the three groups of samples.

Example 3: Clinical Testing on Human Breast and Ovarian Cancer Sample Sets

Samples were blood samples from healthy donors and from people suffering either from breast or ovarian cancer.

Ovarian Cancer

A set of serum samples from patients having clear cell carcinoma and controls was formed as follows:

TABLE 3

| Type | Number |
|---|---|
| Clear Cell Carcinoma (ovarian cancer) | 13 |
| Controls | 10 |
| Total: | 23 |

Those samples were tested according to a method of the invention as described in Example 2. Control unrelated peptides were added to test the selectivity of the assay. One way ANOVA analysis is applied to the results. The same analysis was repeated by an independent laboratory and results are presented in FIG. 1 for 4 control samples versus 4 ovarian carcinoma. A few cases which were supposed to be ovarian cancer samples were showing up as control in the assay according to the invention. After further investigations into sample data and records, it appeared that these samples in fact belonged to ovarian cancer patients in remission. Therefore, it showed that the accuracy of the assay was indeed correct in classifying these samples as non-cancer samples.

A further set of serum samples from patients having clear cell carcinoma (ovarian cancer) and controls was formed as follows:

TABLE 4

| Type | Number |
|---|---|
| Clear Cell Carcinoma (ovarian cancer) | 11 |
| Breast Cancer (CBV) | 2 |
| Benign Ovarian Condition (BOV) | 10 |
| Benign Breast Condition (BBV) | 5 |
| Control healthy women (GVABB) | 5 |
| Total: | 33 |

Results were statistically analyzed as described in Zhou et al., 2002, *Statistical Methods in diagnostic medicines*, Wiley, N.Y. for determining the specificity and sensitivity of the assay. The robustness of the assay and method according to the invention can be summarized as follows:

TABLE 5

|  | Number of positive samples | Number of Negative samples | Total of samples |
|---|---|---|---|
| FALSE | 6 (FP) | 0 (FN) | 6 |
| TRUE | 12 (TP) | 15 (TN) | 27 |
| Total | 18 | 15 | 33 |

Among the false positive, 2 breast cancers and 2 benign breast conditions were detected positive. Assuming True Positive (TP), True Negative (TP), False Positive (FP); False Negative (FN), the specificity and sensitivity of the assay according to the invention are calculated as follows:

Specificity=TN/(TN+FP) and
Sensitivity=TP/(TP+FN).

which leads to 71.4% specificity, 100% sensitivity. Therefore, an assay according to the invention presents very high selectivity and sensitivity values for the detection of ovarian cancers and was able to discriminate between ovarian cancer patients and ovarian cancer patient under remission.

Breast Cancer

A set of serum samples from patients having breast cancer (CBV), breast cysts (BBV), benign ovarian cyst (BOV) and controls was formed as indicated in Table 7 below:

TABLE 6

| Type | Number |
|---|---|
| Breast Cancer (CBV) - "patient" | 66 |
| Benign Breast Condition (BBV) - "healthy" | 54 |
| Benign Ovarian Condition (BOV) - "healthy" | 50 |
| Control healthy women (GVABB) - "healthy" | 20 |
| Total: | 190 |

Among the patients, 29% are younger than 50-year-old and 71% are 50-year old or older. Those samples were tested according to a method of the invention as described in Example 2. Control unrelated peptides (references 1-5) were added to test the selectivity of the assay. Each measurement was performed in triplicate. Reproducibility of the data was assessed by analyzing the standard deviation and the coefficient of variation for all triplicates. Almost all the measured coefficients of variation are below 10% and most are below 5%, indicating good reproducibility. Principal component analysis (PCA) was applied to the data, the p-values obtained by Wilcoxon test (Pepe, 2003, above) and the area under the curve values (AUC for a receiver operating curve (ROC)) are mentioned for each peptide used in the assay under Table 7 below. The lower the p-value, the better the performance of the respective peptide. The higher the AUC above 0.54, the more accurate is the assay.

TABLE 7

| Peptide | p-Value | AUC |
|---|---|---|
| SEQ ID NO: 1 | 9.4e-7 | 0.72 |
| SEQ ID NO: 2 | 6.0e-5 | 0.68 |
| SEQ ID NO: 3 | 6.5e-12 | 0.8 |
| SEQ ID NO: 4 | 1.4e-9 | 0.77 |
| SEQ ID NO: 5 | 4.4e-13 | 0.82 |
| SEQ ID NO: 6 | 0.51 | 0.63 |
| SEQ ID NO: 7 | 1.1e-5 | 0.69 |
| SEQ ID NO: 8 | 0.27 | 0.55 |
| SEQ ID NO: 9 | 0.071 | 0.58 |
| SEQ ID NO: 10 | 0.0036 | 0.63 |
| SEQ ID NO: 11 | 1.9e-5 | 0.69 |
| SEQ ID NO: 12 | 4.2e-6 | 0.7 |
| Reference 1 | 0.64 | 0.52 |
| Reference 2 | 0.77 | 0.51 |
| Reference 3 | 0.95 | 0.5 |

Figure 2:
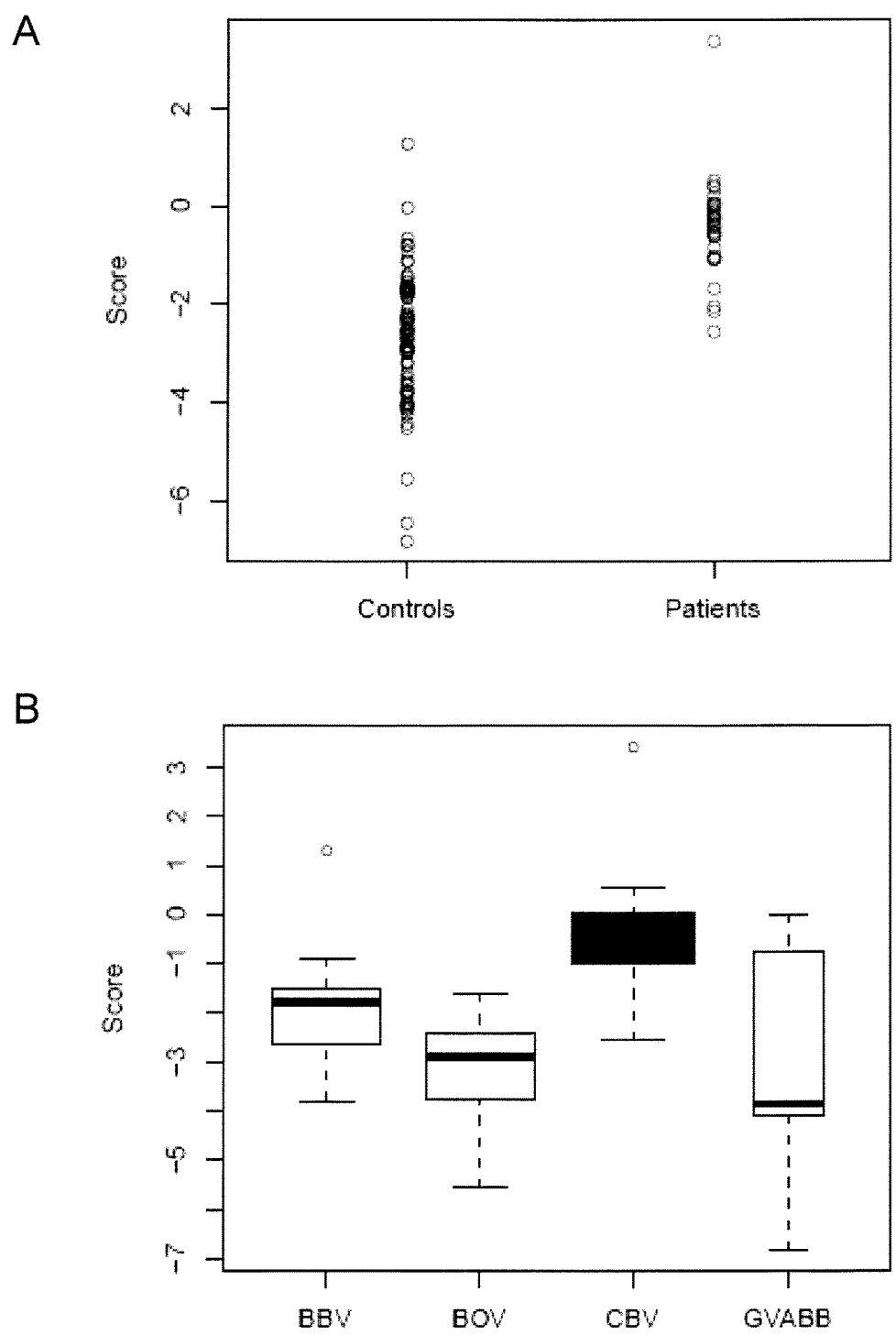
FIG. 2 shows results obtained from the testing set with the Linear Discreet Analysis (LDA) classification method (Friedman, 1989, *Regularized Discriminant Analysis In: Journal of the American Statistical Association,* 84(405): 165-175) on the breast cancer testing set as described in Example 3. The LDA scores obtained lie in the range of −5 to +3 approximately, as illustrated in FIGS. 2A & 2B. BBV=Benign Breast cyst (control); BOV=Benign Ovarian Cyst (control); GVABB=Healthy blood donors (control); CBV=Malignant Breast tumour (Cancer cases).
Figure 2:
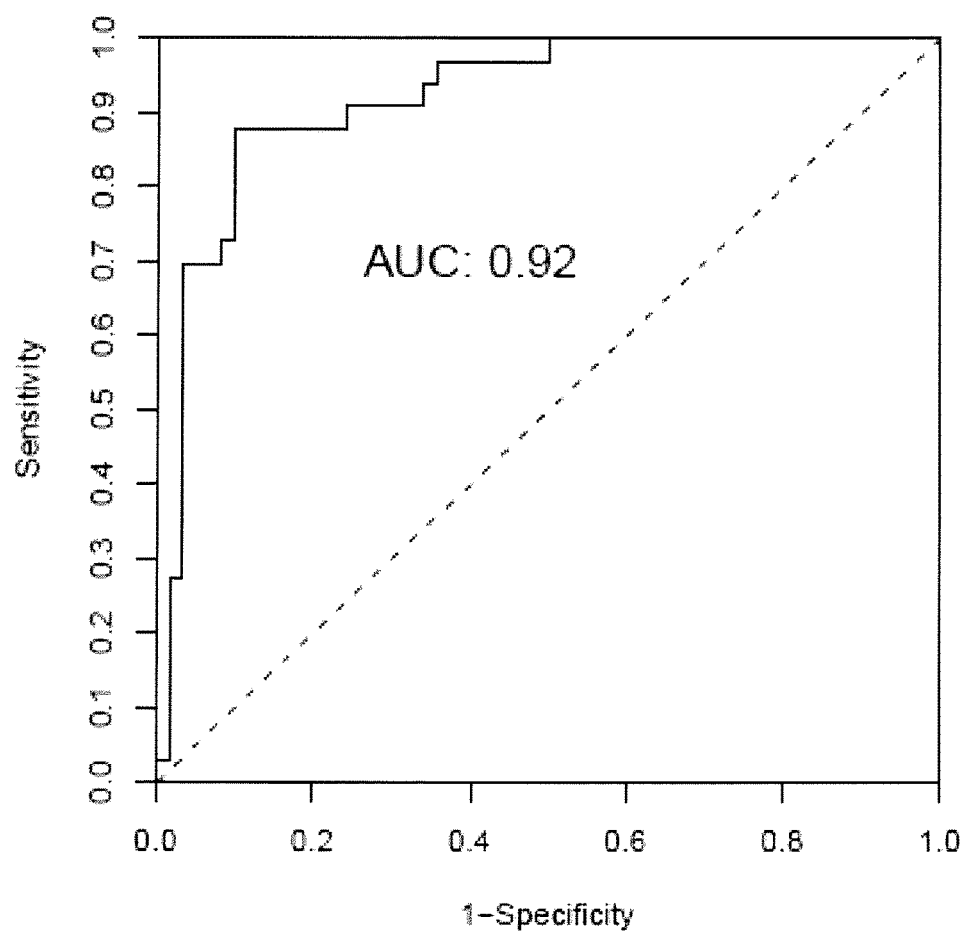

Results were further analyzed using Linear Discriminant Analysis (LDA). The patient data was split in two equal parts, one consisting in a learning set (used to train the classification algorithm), and the other one being a testing set (used to assess the performance of the classifier). Results are presented under FIG. 2. The score obtained with the LDA procedure was used to classify the samples from the testing set. Scores are indicated for cases vs controls (2A), by subgroup (2B), and in the form of a Receiver Operating Characteristic (ROC) curve (2C). The Area Under the Curve (AUC) obtained was 0.92, an excellent value.

A numerical summary of the results obtained for different computed thresholds (1 to 21) is shown in the Table 8 below. The thresholds were chosen uniformly within the range of possible scores (in the range −5 to +5); FP, TP, TN and FN columns contain the respective number of False Positives, True Positives, True Negatives and False Negatives for the given threshold; the sum of these four numbers is always 95 (the total number of samples in the testing set). The specificity and sensitivity given by TN/TN+FP and TP/TP+FN measure the accuracy of the threshold with regards to the total of positive and negative samples in the testing set. The Positive Predictive Value (PPV) and the Negative Predictive Value (NPV) indicate the proportion of patients tested positive (respectively negative) which are correctly diagnosed, and are calculated as TP/TP+FP and TN/TN+FN.

TABLE 8

|    | Threshold | FP | TP | TN | FN | Spec. | Sens. | PPV  | NPV  |
|----|-----------|----|----|----|----|-------|-------|------|------|
| 1  | −5.35     | 62 | 33 | 0  | 0  | 0.00  | 1.00  | 0.35 | —    |
| 2  | −4.99     | 61 | 33 | 1  | 0  | 0.02  | 1.00  | 0.35 | 1.00 |
| 3  | −4.28     | 60 | 33 | 2  | 0  | 0.03  | 1.00  | 0.35 | 1.00 |
| 4  | −3.58     | 59 | 33 | 3  | 0  | 0.05  | 1.00  | 0.36 | 1.00 |
| 5  | −2.52     | 57 | 33 | 5  | 0  | 0.08  | 1.00  | 0.37 | 1.00 |
| 6  | −2.16     | 52 | 33 | 10 | 0  | 0.16  | 1.00  | 0.39 | 1.00 |
| 7  | −1.81     | 47 | 33 | 15 | 0  | 0.24  | 1.00  | 0.41 | 1.00 |
| 8  | −1.46     | 43 | 33 | 19 | 0  | 0.31  | 1.00  | 0.43 | 1.00 |
| 9  | −1.10     | 39 | 33 | 23 | 0  | 0.37  | 1.00  | 0.46 | 1.00 |
| 10 | −0.75     | 32 | 33 | 30 | 0  | 0.48  | 1.00  | 0.51 | 1.00 |
| 11 | −0.40     | 24 | 32 | 38 | 1  | 0.61  | 0.97  | 0.57 | 0.97 |
| 12 | −0.04     | 21 | 30 | 41 | 3  | 0.66  | 0.91  | 0.59 | 0.93 |
| 13 | 0.31      | 11 | 29 | 51 | 4  | 0.82  | 0.88  | 0.72 | 0.93 |
| 14 | 0.66      | 8  | 29 | 54 | 4  | 0.87  | 0.88  | 0.78 | 0.93 |
| 15 | 1.02      | 5  | 24 | 57 | 9  | 0.92  | 0.73  | 0.83 | 0.86 |
| 16 | 1.37      | 2  | 18 | 60 | 15 | 0.97  | 0.55  | 0.90 | 0.80 |
| 17 | 1.72      | 2  | 11 | 60 | 22 | 0.97  | 0.33  | 0.85 | 0.73 |
| 18 | 2.08      | 1  | 4  | 61 | 29 | 0.98  | 0.12  | 0.80 | 0.68 |
| 19 | 2.43      | 1  | 1  | 61 | 32 | 0.98  | 0.03  | 0.50 | 0.66 |

TABLE 8-continued

|    | Threshold | FP | TP | TN | FN | Spec. | Sens. | PPV  | NPV  |
|----|-----------|----|----|----|----|-------|-------|------|------|
| 20 | 3.14      | 0  | 1  | 62 | 32 | 1.00  | 0.03  | 1.00 | 0.66 |
| 21 | 5.26      | 0  | 0  | 62 | 33 | 1.00  | 0.00  | —    | 0.65 |

In brief, the value measured for each peptide is multiplied by a certain weight, the sum of all these weighted values give the resulting score. As an illustration of this model, "sample A" of breast cancer has a score of 1.29. Table 9 below shows the weights obtained from the selected LDA model as described above for 8 peptides according to the invention and corresponding measurements from those peptides for this sample A. Applying the weights to the eight measurements yields the following results:

TABLE 9

|             | SEQ ID NO: | | | | | | | |
|-------------|------|-------|------|-------|------|--------|------|-------|
|             | 1    | 2     | 3    | 4     | 5    | 6      | 9    | 10    |
| Measurement | 0.59 | 0.49  | 0.23 | 0.50  | 0.32 | 0.34   | 0.60 | 0.38  |
| Weights     | −1.71| 13.11 | 0.94 | −5.89 | 1.05 | −11.86 | 5.83 | −3.37 |
| Combination | −1.00| 6.47  | 0.22 | −2.94 | 0.33 | −3.98  | 3.47 | −1.26 |

The sum of the combined values indeed yields a score of 1.29 (except for rounding errors).

Results for all ovarian samples and controls were statistically analyzed as described in *Zhou et al., 2002, Statistical Methods in diagnostic medicines, Wiley, N.Y.* for determining the specificity and sensitivity of the assay. The robustness of the assay and method according to the invention can be summarized as follows: 87.3% specificity, 80.3% sensitivity, 74.7% positive prediction value, 90.5% negative prediction value.

Therefore, an assay according to the invention presents very high selectivity and sensitivity values for the detection of breast cancer.

The invention claimed is:

1. A kit for detecting one or more autoantibodies associated with a breast cancer or an ovarian cancer in a biological fluid sample of a mammalian subject, the kit comprising a peptide or a combination of peptides coupled to a solid support matrix, wherein the peptide or combination of peptides comprises:
 a) a peptide consisting of the amino acid sequence set forth in SEQ ID NO: 5;
 b) a combination of peptides comprising a peptide consisting of the amino acid sequence set forth in SEQ ID NO: 5 and a peptide consisting of the amino acid sequence set forth in SEQ ID NO: 1, a peptide consisting of the amino acid sequence set forth in SEQ ID NO: 4 and a peptide consisting of the amino acid sequence set forth in SEQ ID NO: 12; or
 c) a combination of peptides comprising 1) a peptide consisting of the amino acid sequence set forth in SEQ ID NO: 5 and 2) at least one peptide consisting of the amino acid set forth in SEQ ID NO: 1 SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 12 or a combination thereof,
 wherein the one or more autoantibodies bind to one or more of the peptides comprised in the kit.

2. The kit of claim 1, wherein the peptide is a peptide consisting of the amino acid sequence set forth in SEQ ID NO: 5.

3. The kit of claim 1, wherein said kit comprises a combination of peptides comprising
 a) a peptide consisting of the amino acid sequence set forth in SEQ ID NO: 5; and
 b) at least one peptide consisting of the amino acid sequence set forth in SEQ ID NO: 1, SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 12 or a combination thereof.

4. The kit of claim 1, wherein said kit comprises a combination of peptides comprising a peptide consisting of the amino acid sequence set forth in SEQ ID NO: 5, a peptide consisting of the amino acid sequence set forth in SEQ ID NO: 1, a peptide consisting of the amino acid sequence set forth in SEQ ID NO: 4 and a peptide consisting of the amino acid sequence set forth in SEQ ID NO: 12.

5. A method for detecting a breast or an ovarian cancer from a biological fluid sample of a mammalian subject comprising the steps of:
 (a) providing a biological fluid sample from a mammalian subject;
 (b) bringing said biological fluid sample into contact with the solid matrix of the kit of claim 1, wherein the contacting is under conditions sufficient for binding an antibody present in said biological fluid sample to said solid matrix through antigen-antibody interactions;
 (c) removing the biological fluid sample from the solid matrix to remove unbound antibody from the surface of said solid matrix; and
 (d) detecting the presence of an antigen-antibody complex bound to said solid matrix,
 wherein the presence of said complex is indicative that the biological fluid sample contains one or more breast or ovarian-cancer associated-endogenous antibodies.

6. The method according to claim 5, wherein the peptide bound to the solid matrix is a peptide consisting of the amino acid sequence set forth in SEQ ID NO: 5.

7. The method according to claim 5, wherein the combination of peptides bound to the solid matrix comprises a peptide consisting of the amino acid sequence set forth in SEQ ID NO: 5 and a peptide consisting of the amino acid sequence set forth in SEQ ID NO: 1, a peptide consisting of the amino acid sequence set forth in SEQ ID NO: 4 and a peptide consisting of the amino acid sequence set forth in SEQ ID NO: 12.

8. The method according to claim 5, wherein the combination of peptides bound to the solid matrix comprises 1) a peptide consisting of the amino acid sequence set forth in SEQ ID NO: 5 and 2) at least one peptide consisting of the amino acid set forth in SEQ ID NO: 1 SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 12 or a combination thereof.

* * * * *